United States Patent
Westlund et al.

(10) Patent No.: US 7,899,551 B2
(45) Date of Patent: *Mar. 1, 2011

(54) MEDICAL LEAD SYSTEM UTILIZING ELECTROMAGNETIC BANDSTOP FILTERS

(75) Inventors: Randy Westlund, River Falls, WI (US); Robert A. Stevenson, Canyon Country, CA (US); Christine A. Frysz, Orchard Park, NY (US); Warren S. Dabney, Orchard Park, NY (US)

(73) Assignee: Greatbatch Ltd., Clarence, NY (US)

( * ) Notice: Subject to any disclaimer, the term of this patent is extended or adjusted under 35 U.S.C. 154(b) by 661 days.

This patent is subject to a terminal disclaimer.

(21) Appl. No.: 11/943,883

(22) Filed: Nov. 21, 2007

(65) Prior Publication Data

US 2008/0132987 A1    Jun. 5, 2008

Related U.S. Application Data

(63) Continuation-in-part of application No. 11/558,349, filed on Nov. 9, 2006, which is a continuation-in-part of application No. 11/423,073, filed on Jun. 8, 2006, which is a continuation-in-part of application No. 10/123,534, filed on Apr. 15, 2002, now Pat. No. 7,844,319.

(60) Provisional application No. 60/283,725, filed on Apr. 13, 2001, provisional application No. 60/597,125, filed on Nov. 11, 2005, provisional application No. 60/803,672, filed on Jun. 1, 2006.

(51) Int. Cl.
*A61N 1/00* (2006.01)

(52) U.S. Cl. ..................................................... 607/122
(58) Field of Classification Search .................. 607/122
See application file for complete search history.

(56) References Cited

U.S. PATENT DOCUMENTS

| | | |
|---|---|---|
| 3,871,382 A | 3/1975 | Mann |
| 3,968,802 A | 7/1976 | Ballis |
| 4,633,181 A | 12/1986 | Murphy-Boesch et al. |
| 4,799,499 A | 1/1989 | Bisping |
| 4,858,623 A | 8/1989 | Bradshaw et al. |
| 5,209,233 A | 5/1993 | Holland et al. |
| 5,217,010 A | 6/1993 | Tsitlik et al. |
| 5,246,438 A | 9/1993 | Langberg |
| 5,300,108 A | 4/1994 | Rebell et al. |
| 5,333,095 A | 7/1994 | Stevenson et al. |
| 5,363,845 A | 11/1994 | Chowdhury et al. |

(Continued)

FOREIGN PATENT DOCUMENTS

EP    0 498 996 B1    3/1997

(Continued)

*Primary Examiner*—George Manuel
(74) *Attorney, Agent, or Firm*—Kelly Lowry & Kelley, LLP (57) ABSTRACT

Medical lead systems utilizing electromagnetic bandstop filters are provide which can be utilized in a magnetic resonance imaging (MRI) environment for patients who have implanted medical devices. Such lead systems may be advantageously used in left ventricle cardiac stimulation systems, neurostimulation systems, and deep brain electrodes used for the treatment of Parkinson's disease and other movement disorders. The bandstop filters, which include a tuned parallel capacitor and inductor circuit, are backwards compatible with known implantable deployment systems.

25 Claims, 12 Drawing Sheets

U.S. PATENT DOCUMENTS

| | | | |
|---|---|---|---|
| 5,398,683 A | 3/1995 | Edwards et al. |
| 5,514,173 A | 5/1996 | Rebell et al. |
| 5,545,201 A | 8/1996 | Helland et al. |
| 5,629,622 A | 5/1997 | Scampini |
| 5,697,958 A | 12/1997 | Paul et al. |
| 5,716,390 A | 2/1998 | Li |
| 5,722,998 A | 3/1998 | Prutchi et al. |
| 5,741,321 A | 4/1998 | Brennen |
| 5,751,539 A | 5/1998 | Stevenson et al. |
| 5,759,202 A | 6/1998 | Schroeppel |
| 5,905,627 A | 5/1999 | Brendel et al. |
| 5,959,829 A | 9/1999 | Stevenson et al. |
| 5,964,705 A | 10/1999 | Truwit et al. |
| 5,973,906 A | 10/1999 | Stevenson et al. |
| 5,978,204 A | 11/1999 | Stevenson |
| 6,008,980 A | 12/1999 | Stevenson et al. |
| 6,055,457 A | 4/2000 | Bonner |
| 6,101,417 A | 8/2000 | Vogel et al. |
| 6,141,594 A | 10/2000 | Flynn et al. |
| 6,159,560 A | 12/2000 | Stevenson et al. |
| 6,275,369 B1 | 8/2001 | Stevenson et al. |
| 6,280,385 B1 | 8/2001 | Melzer et al. |
| 6,424,234 B1 | 7/2002 | Stevenson |
| 6,456,481 B1 | 9/2002 | Stevenson |
| 6,473,291 B1 | 10/2002 | Stevenson |
| 6,493,591 B1 | 12/2002 | Stokes |
| 6,529,103 B1 | 3/2003 | Brendel et al. |
| 6,535,766 B1 | 3/2003 | Thompson et al. |
| 6,539,253 B2 | 3/2003 | Thompson et al. |
| 6,566,978 B2 | 5/2003 | Stevenson et al. |
| 6,567,259 B2 | 5/2003 | Stevenson et al. |
| 6,567,703 B1 | 5/2003 | Thompson et al. |
| 6,606,513 B2 | 8/2003 | Lardo et al. |
| 6,643,903 B2 | 11/2003 | Stevenson et al. |
| 6,675,033 B1 | 1/2004 | Lardo et al. |
| 6,675,779 B2 | 1/2004 | King et al. |
| 6,687,550 B1 | 2/2004 | Doan |
| 6,701,176 B1 | 3/2004 | Halperin et al. |
| 6,765,780 B2 | 7/2004 | Brendel et al. |
| 6,847,837 B1 | 1/2005 | Melzer et al. |
| 6,868,288 B2 | 3/2005 | Thompson |
| 6,876,885 B2 | 4/2005 | Swoyer et al. |
| 6,882,248 B2 | 4/2005 | Stevenson et al. |
| 6,898,454 B2 | 5/2005 | Atalar et al. |
| 6,925,328 B2 | 8/2005 | Foster et al. |
| 6,931,286 B2 | 8/2005 | Sigg et al. |
| 6,949,929 B2 | 9/2005 | Gray et al. |
| 6,952,613 B2 | 10/2005 | Swoyer et al. |
| 6,971,391 B1 | 12/2005 | Wang et al. |
| 6,985,347 B2 | 1/2006 | Stevenson et al. |
| 6,999,818 B2 | 2/2006 | Stevenson et al. |
| 7,013,180 B2 | 3/2006 | Dougherty et al. |
| 7,092,766 B1 | 8/2006 | Salys et al. |
| 7,113,387 B2 | 9/2006 | Stevenson et al. |
| 7,123,013 B2 | 10/2006 | Gray |
| 7,155,271 B2 | 12/2006 | Halperin et al. |
| 2003/0028094 A1 | 2/2003 | Kumar et al. |
| 2003/0050557 A1 | 3/2003 | Susil et al. |
| 2004/0167392 A1 | 8/2004 | Halperin et al. |
| 2004/0263174 A1 | 12/2004 | Gray et al. |
| 2005/0197677 A1 | 9/2005 | Stevenson |
| 2006/0009819 A1 | 1/2006 | Przybyszewski |
| 2006/0100506 A1 | 5/2006 | Halperin et al. |

FOREIGN PATENT DOCUMENTS

| | | |
|---|---|---|
| JP | 60141034 | 7/1985 |
| JP | 61181925 | 8/1986 |
| JP | 62233905 | 10/1987 |
| JP | 4071536 | 3/1992 |
| JP | 6054823 | 3/1994 |
| JP | 11239572 | 9/1999 |
| WO | WO 99/19739 A1 | 4/1999 |
| WO | WO 02/083016 A1 | 10/2002 |

FIG. 1

| French Guage | Diameter (mm) | Diameter (inches) |
|---|---|---|
| 3 | 1 | 0.039 |
| 4 | 1.35 | 0.053 |
| 5 | 1.67 | 0.066 |
| 6 | 2 | 0.079 |
| 7 | 2.3 | 0.092 |
| 8 | 2.7 | 0.105 |
| 9 | 3 | 0.118 |
| 10 | 3.3 | 0.131 |
| 11 | 3.7 | 0.144 |
| 12 | 4 | 0.158 |
| 13 | 4.3 | 0.170 |
| 14 | 4.7 | 0.184 |
| 15 | 5 | 0.197 |
| 16 | 5.3 | 0.210 |
| 17 | 5.7 | 0.223 |
| 18 | 6 | 0.236 |
| 19 | 6.3 | 0.249 |
| 20 | 6.7 | 0.263 |
| 22 | 7.3 | 0.288 |
| 24 | 8 | 0.315 |
| 26 | 8.7 | 0.341 |
| 28 | 9.3 | 0.367 |
| 30 | 10 | 0.393 |
| 32 | 10.7 | 0.419 |
| 34 | 11.3 | 0.455 |

MEDICAL LEAD SYSTEM UTILIZING ELECTROMAGNETIC BANDSTOP FILTERS

BACKGROUND OF INVENTION

Magnetic resonance imaging (MRI) is currently contraindicated for patients who have implanted medical devices. This is due largely to the patient safety issue that results when the strong electromagnetic fields of an MRI system interact with the antenna-like therapy delivery leads of an active implantable medical device (AIMD). It is well documented that the radio frequency (RF) signals that are generated by the MRI system can couple along the length of a lead body and create induced current loops. These current loops can cause significant heating at points of high current concentration, the most significant of which is the distal tip, where the lead system makes direct contact with body tissue.

As disclosed in U.S. patent application Ser. No. 11/558, 349, filed Nov. 9, 2006, TANK FILTERS PLACED IN SERIES WITH THE LEAD WIRES OR CIRCUITS OF ACTIVE MEDICAL DEVICES TO ENHANCE MRI COMPATIBILITY, and Provisional Patent Application No. 60/968, 662, filed Aug. 29, 2007, entitled A CYLINDRICAL BAND STOP FILTER FOR M LEAD SYSTEMS, the contents of which are incorporated herein by reference, a novel method to minimize the expected heating at the distal tip of the lead system is to incorporate a bandstop filter. This bandstop filter is comprised of an inductor and capacitor in parallel, with the entire filter connected in series to the lead system. In such a system, the bandstop filter can be constructed so that its resonant frequency or frequencies coincides with the RF operating frequency of one or more MRI systems.

RF frequencies are directly related to the MRI machine static magnetic field by the Lamour Relationship. Typical values are 64 MHz for 1.5 T systems, and 128 MHz for 3.0 T systems. At resonance, the impedance of the bandstop filter is quite high which reduces the flow of current at the MRI RF pulsed frequency thereby reducing leadwire and/or electrode heating. Increasing the impedance at the distal tip also greatly reduces the amount of RF current that would flow into body tissue. It has been documented that excess current can cause tissue damage or even tissue necrosis.

Implementation of this technology in implantable leads is a significant challenge. Bandstop filters for use in lead systems must be biocompatible, not significantly change the electrical performance characteristics of the lead (except within the context of the invention), and must not significantly affect size, weight, or implantability. With increasingly smaller leads being developed to accommodate small vasculature and left ventricular pacing through the coronary sinus, bandstop technology must be equally scalable to match the same demands.

The present invention satisfies these needs and provides other related advantages.

SUMMARY OF THE INVENTION

The present invention relates to medical lead systems which utilize electromagnetic bandstop filters. Such medical lead systems are advantageously utilized in a magnetic resonance imaging (MRI) environment for patients who have implanted medical devices.

The medical lead system of the present invention includes a lead wire configured for insertion into a venous system. The lead wire includes a terminal pin at one end for connecting the lead system to the implantable medical device. An electrode is provided at an opposite end, which is in contact with biological cells. The bandstop filter associated with the lead wire attenuates current flow through the lead wire at a selected frequency. The bandstop filter comprises a capacitor in parallel with an inductor. The parallel capacitor and inductor are placed in series with the lead wire. Values of capacitance and inductance are selected such that the bandstop filter is resonant at selected MRI frequencies.

In a preferred form, the lead wire comprises a proximal section extending from the terminal pin, and a reduced-diameter distal section. The bandstop filter is disposed between the proximal and distal sections. Moreover, the bandstop filter may include tines for fixing the bandstop filter in a desired location within the venous system.

As illustrated, the lead wire may comprise an epicardial lead, a split-cylinder cuff electrode, self-sizing nerve cuffs, a multiple cuff nerve electrode, a multiple bandstop filter array, or a deep brain probe. In each instance, the bandstop filter is incorporated therein.

More particularly, in one form, the multiple bandstop filter array comprises a plurality of bandstop filter chips disposed on a substrate. At least one of the bandstop filter chips may be thick-film deposited onto the substrate. Where the lead wire comprises a deep brain probe, a flexible conductor may be disposed between the bandstop filter and the electrode.

It will be appreciated that such lead systems may be advantageously used in left ventricle cardiac stimulation systems, neuro-stimulation systems, and in connection with deep brain electrodes used for the treatment of Parkinson's Disease and other movement disorders. The bandstop filters, which include a tuned parallel capacitor and conductor circuit, are backwards compatible with known implantable deployment systems.

Other features and advantages of the present invention will become apparent from the following more detailed description, taken in connection with the accompanying drawings which illustrate, by way of example, the principles of the invention.

DETAILED DESCRIPTION OF THE PREFERRED EMBODIMENTS

The present invention addresses three primary topics which include: (1) left ventricle cardiac stimulation with a proximal bandstop filter; (2) neurostimulation with various types of neuro-cuffs employing a bandstop filter; and (3) deep brain electrodes that are used for treatment of Parkinson's Disease and other movement disorders such as tremor and dystonia, depression and neurological disorders.

Figure 1:
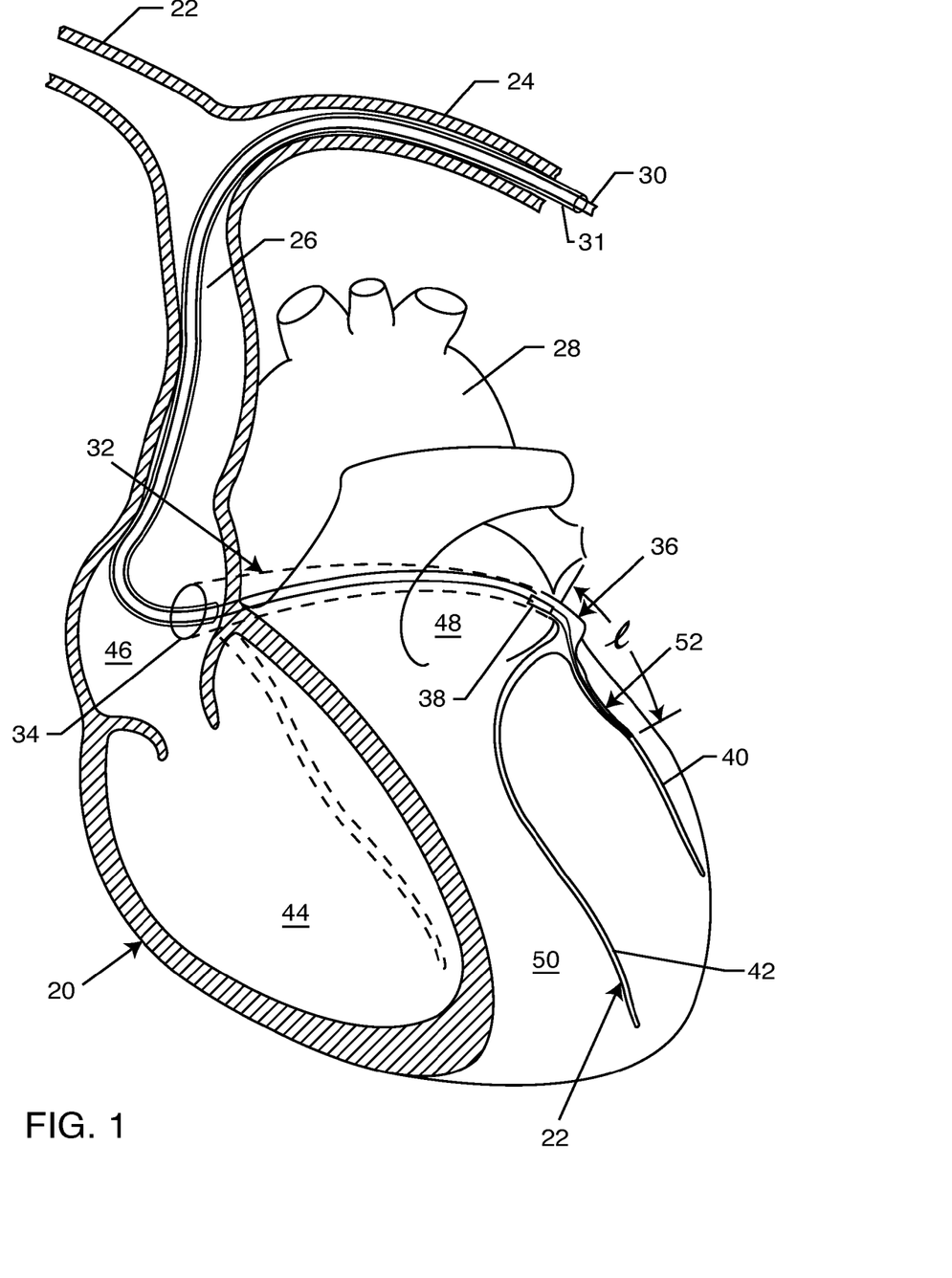
FIG. 1 is a diagrammatic representation of the human heart, showing a left ventricular endocardial lead system embodying the present invention.

FIG. 1 is a diagrammatic representation of a human heart 20 which includes right and left subclavian veins 22 and 24 respectively, the superior vena cava 26 and the aorta 28. A lead wire 30, which is typically routed from a biventricular cardiac pacemaker or a biventricular implantable cardioverter defibrillator (ICD) (which are not shown), is routed through a catheter 31 and directed, in this case, through the left subclavian vein 24 and then down through the superior vena cava 26 and into the coronary sinus 32. The leadwire 30 must first enter the coronary sinus ostium 34 where the implanting physician selects the correct location. The coronary sinus 32 is actually divided into two zones: the first part (on the left) is known as the coronary sinus 32; and the second part (on the right) is called the great cardiac vein 36. The great cardiac vein 36 wraps around the back of the left ventricle. The bandstop filter 38 of the present invention is intended to be placed ideally near the end of the great cardiac vein 36 where it breaks into several venous branches. These branches are called the posterior branch, the lateral branch 40 and the anterior branch 42. A more comprehensive name, for example, would be the interventricular branch.

Figure 1A:
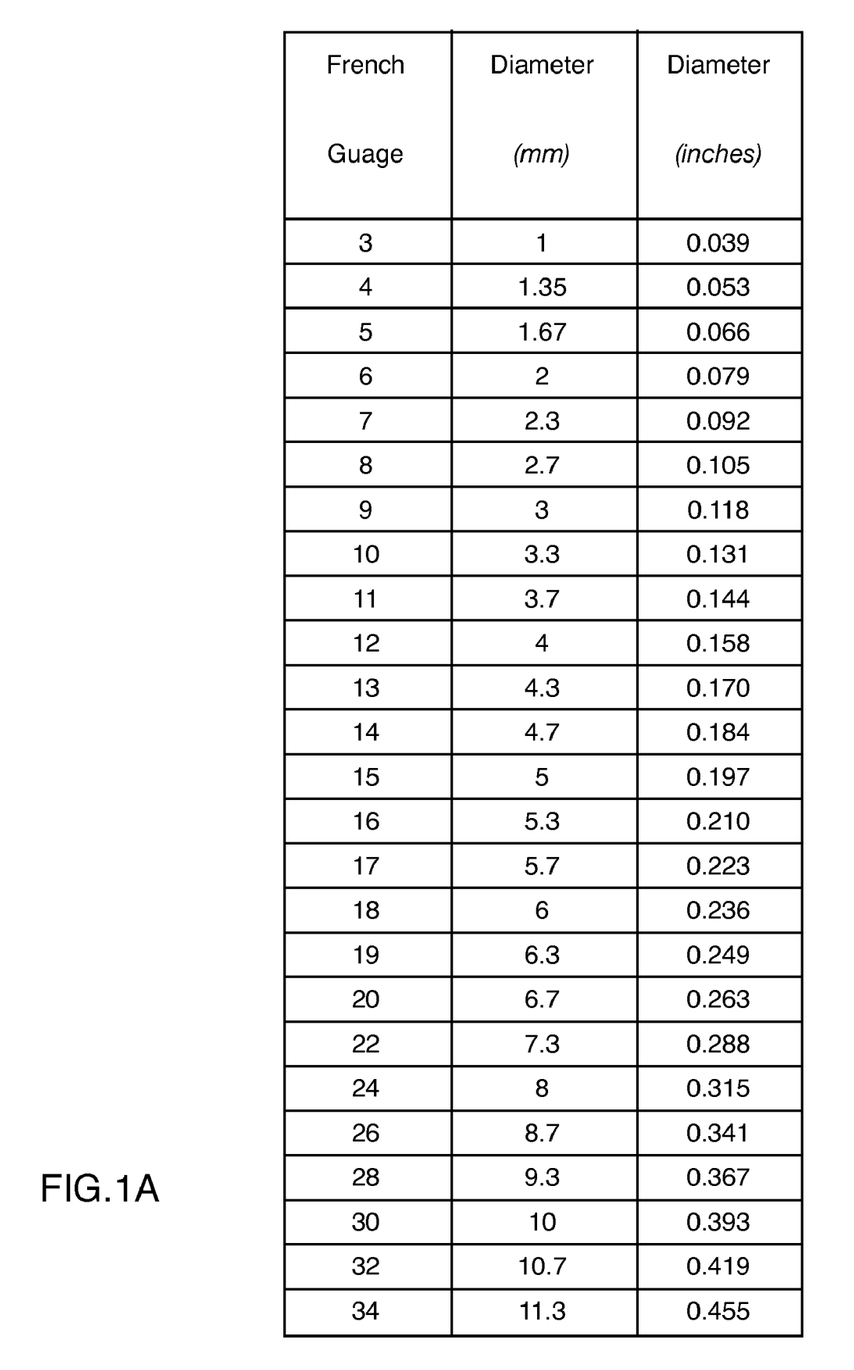
FIG. 1A is a table showing the relationship between French sizes and millimeters and inches.

Referring once again to FIG. 1, one can also see the right ventricle 44 and the right atrium 46. Also shown are the left atrium 48 and the left ventricle 50. The ideal location for a proximal bandstop filter 38 is shown. An ideal length for the proximal bandstop filter 38 would be between 5 and 7.5 mm in length. At this particular location, at the end of the great cardiac vein 36, cardiac motion is relatively small and fibrotic tissue will tend to encapsulate the bandstop filter 38 and its lead wires 30 and thereby attach it/fixate it in position in this relatively low motion region. This is a particular advantage to the present invention, in that the lead 30 will remain highly reliable and resistant to breakage. Because of the relatively large diameter of the coronary sinus 32 and the great cardiac vein 36, this portion of the lead wire system, including the bandstop filter 38, can be of much larger diameter (for example, 7 or 8 French). Beyond this point, where the great cardiac vein 36 branches, the venous systems become much smaller. In general, these branches are below 6 French in diameter and ideal electrode sizes go all the way down to 3 French. FIG. 1A shows the relationship between French size, millimeters and inches. Since left ventricular pacing is important for cardiac resynchronization and treatment of congestive heart failure, it is a feature of the present invention that a lead wire reduction occurs at the point of egress of the bandstop filter 38 allowing insertion of electrodes into the small diameter venous system in the proper position outside the left ventricle 50.

The primary benefit of locating the bandstop filter 38 in the coronary sinus 32 and/or great cardiac vein 36 is that the diameter of the bandstop filter 38 itself can be larger making it much easier to manufacture. The distal portion 52 of the lead 30 from the bandstop filter 38 is smaller (3 to 6 French size) for easier employment and navigation into the branch veins of the left ventricle 50. Secondary benefits beyond the diameter of the bandstop filter 38 include the length of the bandstop filter. Entering into and navigating the coronary sinus 32 and great cardiac vein 36 generally involve larger bend radii compared to accessing and navigating the branch vessels. Therefore the portion of the lead 52 that traverses through and resides in the branch vessels must be very small and very flexible, not having a stiff section longer than approximately 1.5 mm as a rule of thumb. Rigid sections of the lead 30 measuring longer than 1.5 mm can impede the ability to navigate around the tight corners and bends of the branch vessels. In the coronary sinus 32 and great cardiac vein 36, however, there is substantially more latitude, and stiff sections of the lead could approach 5 mm or even 7.5 mm without drastically impeding deliverability. A secondary benefit of locating the bandstop filter 38 in the coronary sinus 32 or the great cardiac vein 36 has to do with MRI image artifacts. Although the image artifact will be quite small due to avoiding the use of ferromagnetic materials, it is still beneficial to locate the bandstop filter 38 away from the coronary arteries, ventricular wall motion or other anatomies/physiologies/pathologies of most interest. If a bandstop filter 38 is located in the coronary sinus 32, however, it could generate small artifact in the vicinity of the valves. Another benefit of having the bandstop filter 38 located in the coronary sinus 32 or the great cardiac vein 36 is that its rigidness provides a foundation on which fixation fixtures may be more strategically utilized. For example, one or more tines could originate from the region of the lead where the bandstop filter 38 resides. Additionally, rigidness of the bandstop filter 38 makes the tines more effective in their engagement of the vessel walls. Alternatively, a rigid portion of the lead 30, skillfully navigated beyond a corner or bifurcation, can function as a fixation mechanism that proves difficult or requires skill to track the lead.

Figures 2, 2A:
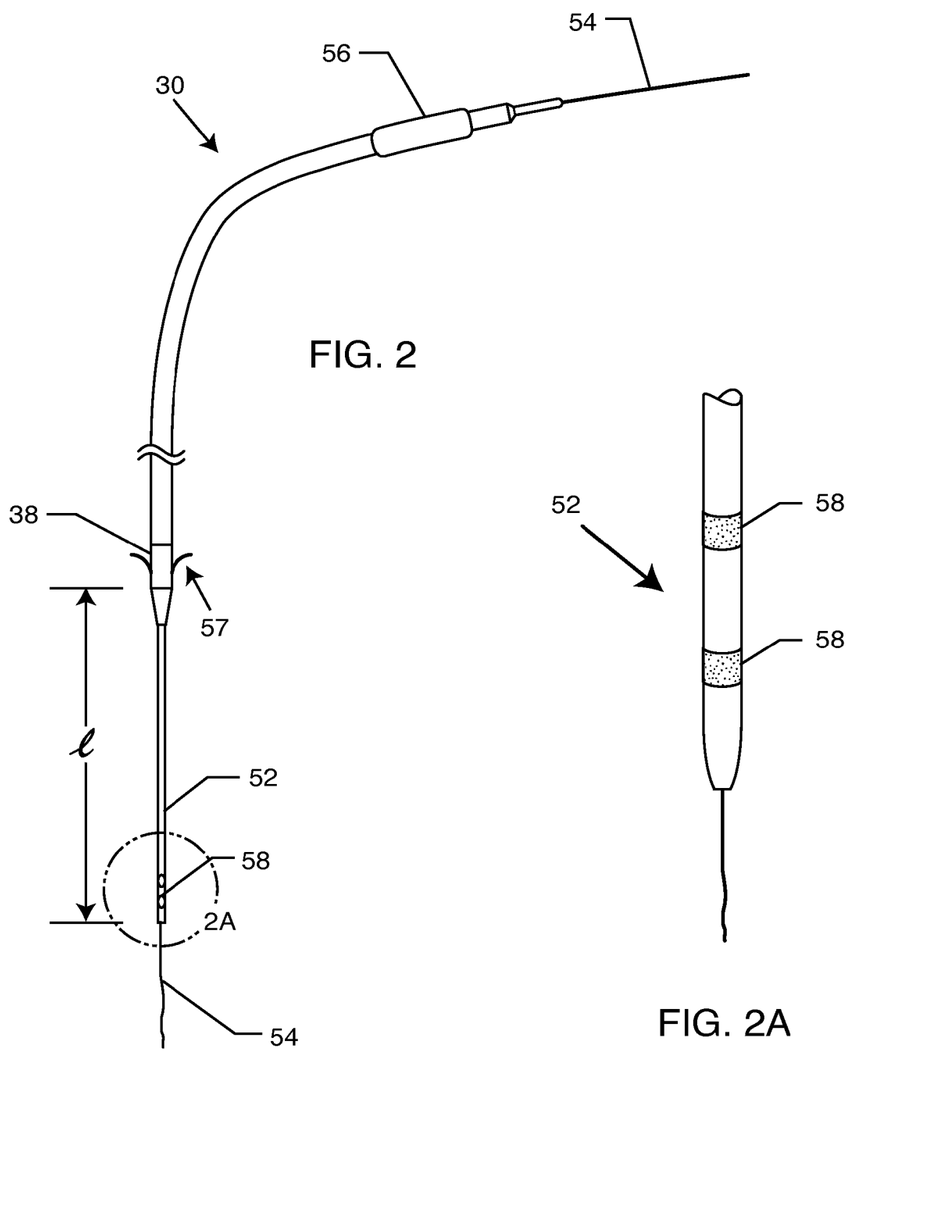
FIG. 2 is an enlarged perspective view of the lead system of FIG. 1.
FIG. 2A is an enlarged view of the distal lead taken generally of the area indicated by the line 2A in FIG. 2.

FIG. 2 is an enlarged perspective view of the lead wire system 30 taken from FIG. 1. One can see that there is a guide wire 54 which is common in the prior art for inserting into position prior to sliding the lead wire system 30 down over it. A terminal pin 56 is designed to plug into the implantable medical device, such as a pacemaker or ICD. The bandstop filter 38 is shown at the point where the lead wire 30 would be reduced from 6-9 French down to 3-6 French. Optional fixation tines 57 are shown which may be affixed to the bandstop filter 38. By way of reference, the French scale is related to both diameter in millimeters (mm) or inches. For example, 7 French is 2.3 mm (0.092 inch) in diameter and 3 French is only 1 mm in diameter (0.039 inch). The length (l) of the reduced diameter lead wire section 52 can be adjusted in accordance with the branch vein into which the lead system is being inserted in the desired location of the electrodes 58. Below the electrodes 58 is the other end of the guide wire 54. Once the electrodes 58 are in the proper position and the system has been tested, the guide wire 54 is typically removed. A particular advantage of the lead system 30 as shown in FIG. 2 is that no new deployment instruments or catheters are required. In other words, this system that includes the bandstop filter 38 is backwards compatible with all known deployment systems. It is also very important that the lead wire system 30 is designed to be extracted in the case of a broken lead, defective lead or infected lead. The lead wire system illustrated in FIGS. 2 and 2A, is also backwards compatible with current (prior art) mechanical and laser lead extraction technologies.

Figure 3:
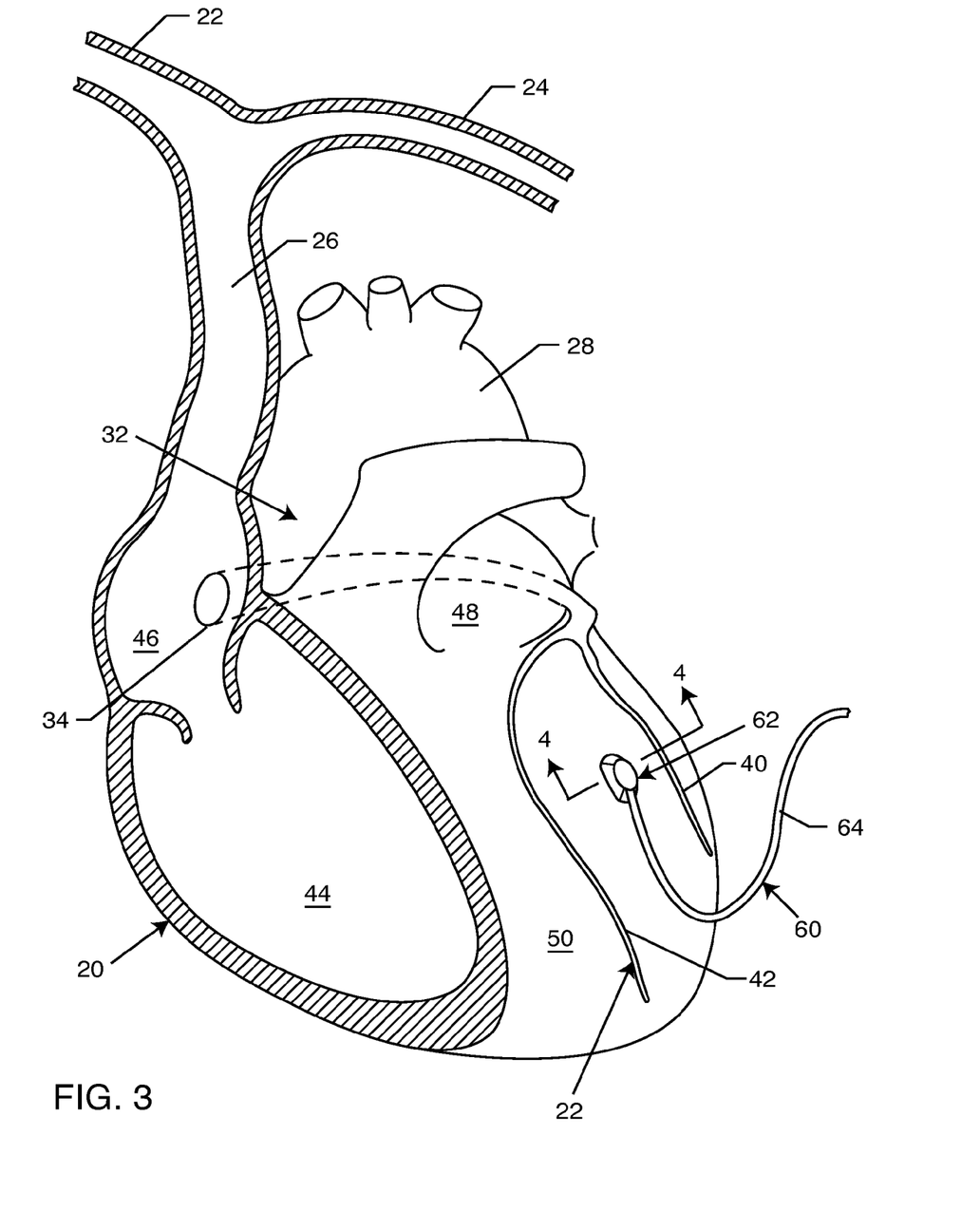
FIG. 3 is a diagrammatic representation of the human heart, showing epicardial leadwire attachment to the outside of the left ventricle in accordance with the present invention.

FIG. 3 is a diagrammatic representation of the human heart similar to that illustrated in FIG. 1. However, in this case, external (epicardial) electrodes 62 are attached outside and to the left ventricle 50 by means of epicardial leads 60. A sutureless myocardial lead 60, 64 is shown affixed to the outside of the left ventricle. This methodology is well known and generally involves an insertion between the ribs outside of the heart and a screwdriver type feature to affix the sutureless epicardial lead tip electrode 62 in place. Epicardial leads may also have a suture feature which is also well known in the art, which can have a helical or other configuration type tip. It will be obvious to those skilled in the art that the present invention can be extended to any type of external (epicardial) electrode 62 or satellite pacer affixed to the outside of the heart, particularly outside of the left ventricle.

Figure 4:
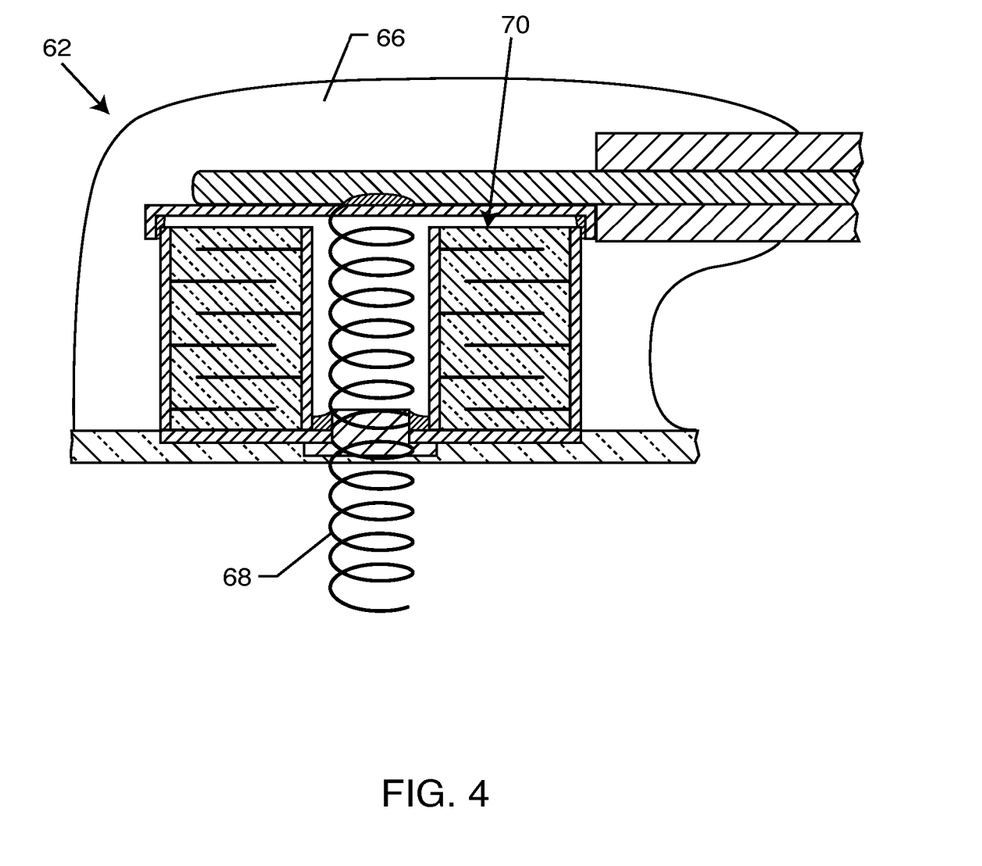
FIG. 4 is a cross-sectional view of an epicardial lead embodying the bandstop filter of the present invention taken generally along the line 4-4 in FIG. 3.
Figure 12:
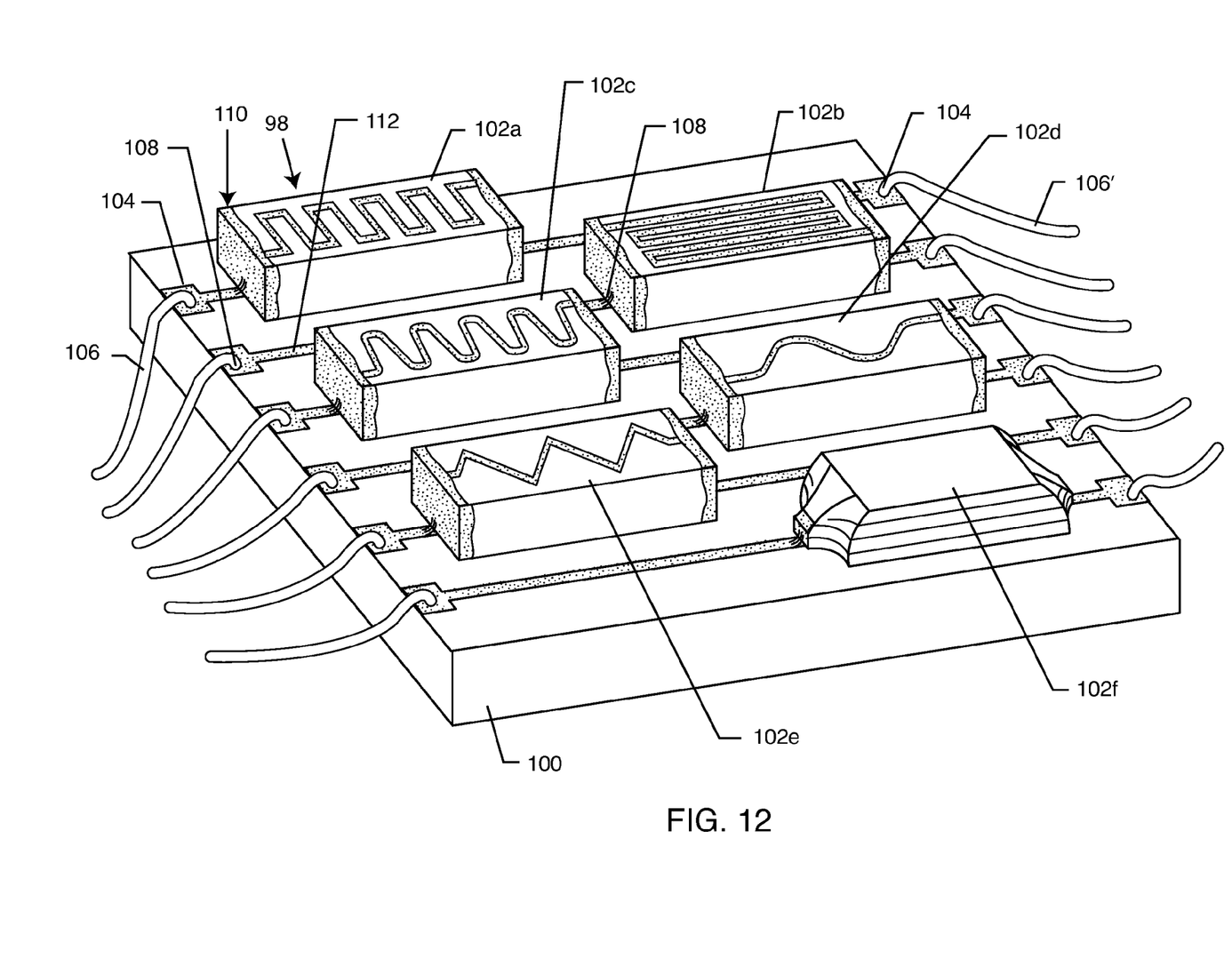
FIG. 12 is an exposed perspective view of one of many possible variations of the multiple bandstop filter array of FIG. 10.

FIG. 4 is a cross-sectional view taken generally along line 4-4 of FIG. 3, illustrating an epicardial lead electrode assembly 62 which includes a bandstop filter 70. In the prior art, the epicardial lead electrode assembly 62 is typically overmolded with silicone rubber 66. The assembly shown in FIG. 4 is self-affixing to the myocardial tissue by a helical electrode structure 68. Typically this electrode is affixed into the myocardium by 3½ mechanical turns and is made of platinum-iridium alloy or equivalent biocompatible material. The helical electrode tip 68 is affixed into the myocardial tissue by a screwdriver type turning surgical tool. The bandstop filter 70, as illustrated in FIG. 4, is taken generally from FIG. 42 of U.S. patent application Ser. No. 11/558,349, filed Nov. 9, 2006. It will be obvious to those skilled in the art that almost all of the other novel bandstop filter embodiments that are disclosed in U.S. patent application Ser. No. 11/558,349 can be incorporated into the epicardial lead 62 in FIG. 4. For example the bandstop filters shown in U.S. patent application Ser. No. 11/558,349, FIGS. 35, 37, 42, 58, 65, 69, 70, 80, 85, 87, 94, 115, 118, 128, 130, 132, 133, 141, 142, 149, 151, 156, 157 are all readily adaptable into the bandstop filter 38 and 70 as illustrated in FIGS. 12 and 4 (any of the designs in U.S. patent application Ser. No. 60/968,662, filed Aug. 29, 2007, are also applicable).

Figure 5:
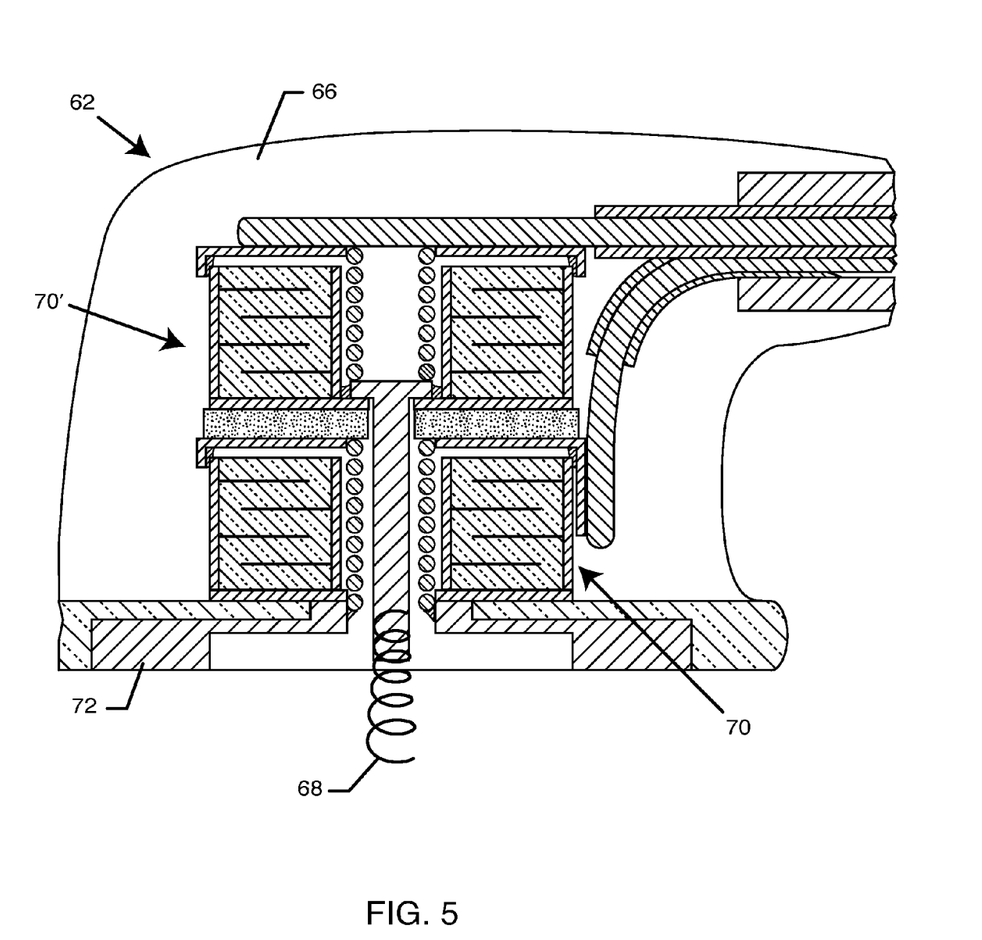
FIG. 5 is an alternative epicardial lead tip taken generally along the line 4-4 in FIG. 3.

FIG. 5 is very similar to the epicardial lead electrode assembly 62 described in FIG. 4, except that it has a novel ring structure 72 associated with a bandstop filter chip 70. This epicardial bipolar electrode also has a bandstop filter chip 70' in series with its helical tip electrode 68. Not shown, but obvious to those skilled in the art, is that a screwdriver type head mechanism can be added for convenient adapting to prior art deployment instruments. As previously mentioned, any of the cylindrical bandstop filter chips as described in U.S. patent application Ser. No. 60/968,662, filed Aug. 29, 2007, can also readily adapted to any of the novel bandstop filter applications as described herein.

Figures 6, 7:
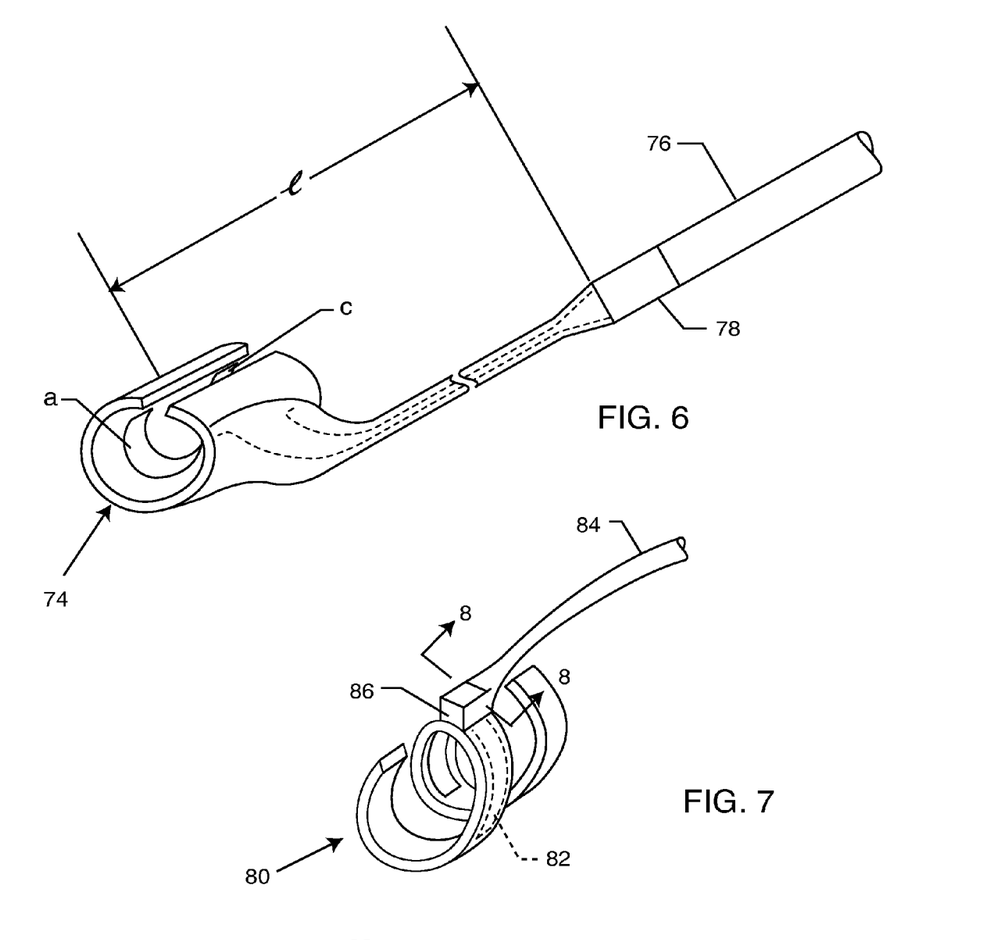
FIG. 6 illustrates a split cylinder cuff electrode designed to wrap around a nerve.
FIG. 7 illustrates a self-sizing helical cuff coil including the bandstop filter chip of the present invention.

FIG. 6 illustrates a split cylinder cuff electrode 74 embodying two electrodes (Anode (a) and Cathode (c)). This is designed to be inserted by a physician around a nerve. It is a bipolar system typically consisting of a 6-8 French diameter lead body 76. A double bandstop filter chip 78 (two discrete bandstop filter chips in parallel) in accordance with the present invention is located as shown. In general, the cuff 74 is sized to match the diameter of the nerve which passes through its center. The lead body 76, after the double bandstop filter 78, is of a reduced diameter, generally in the 3-4 French range. Not shown is a closing suture which is typically used to draw the cuff together after it's installed.

FIG. 7 illustrates helical nerve cuffs 80 which are self-sizing. These incorporate electrode foils 82 which are well known in the prior art. The lead body 84 is attached to a bandstop filter 86 of the present invention. This can be unipolar or bipolar as shown. The electrode foil 82 can either be etched or stamped and then the termination point where the conductor attaches to the foil is either prepared or fabricated. This is the location to where the bandstop filter 86 is electrically attached and incorporated. The conductors and the foil 82 on the bandstop filter 86 are laid into a split mold and assembled and then silicone is injected into the mold. FIG. 7 illustrates one leg of a bipolar or multipolar lead. Obviously, a bandstop filter 86 would be required for each electrode foil in the multipolar configuration.

Figure 8:
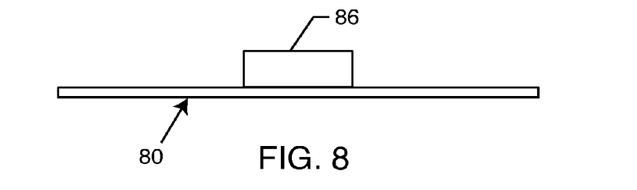
FIG. 8 is a sectional view taken generally along the line 8-8 in FIG. 7.

FIG. 8 is an enlarged sectional view taken generally along line 8-8 of FIG. 7.

Figure 9:
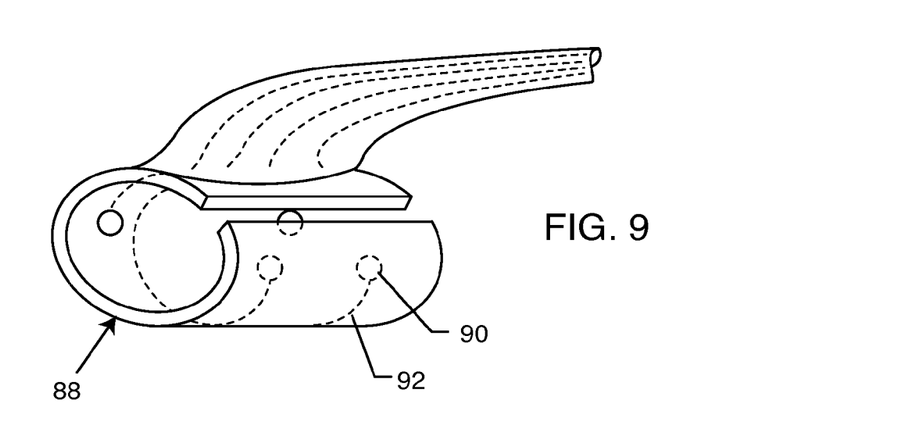
FIG. 9 illustrates a nerve cuff employing a multiplicity of electrodes and bandstop filter chips for a large nerve trunk, in accordance with the present invention.

FIG. 9 illustrates a larger multiple cuff nerve electrode 88 for current steering in a large nerve trunk. Various electrodes can be stimulated by trial and error to obtain the optimal result. For example, for pain control, one can try various electrodes and various types of electrical stimulation by trial and error until pain is minimized or eliminated. The multiple parallel filter electrodes 90, similar to that described in FIG. 4, can be placed in conjunction with each one of the conductors 92 as shown.

Figures 10, 11:
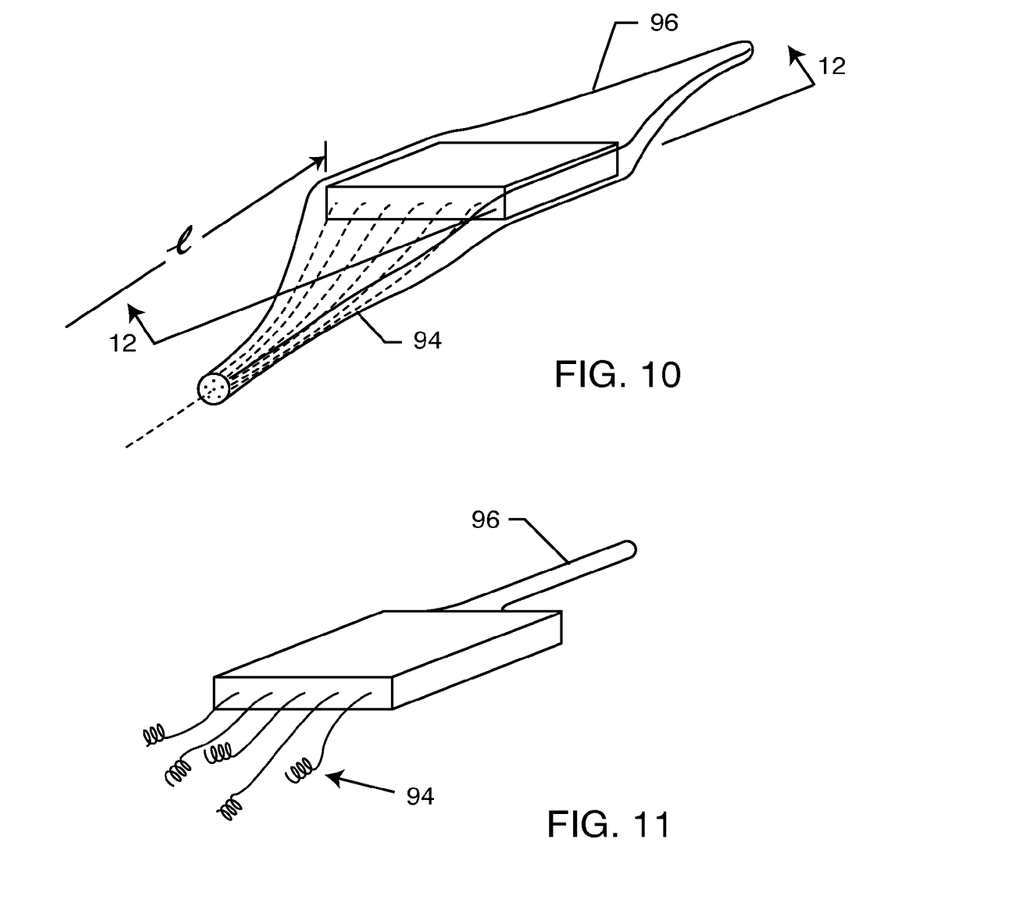
FIG. 10 illustrates one methodology of putting multiple bandstop filter chips in series with the lead wires of the multiple cuff electrode of FIG. 9.
FIG. 11 illustrates a multi-conductor lead body connected to a multiple tank filter chip array that has multiple electrodes, in accordance with the present invention.

FIG. 10 illustrates an alternative in that a multiple bandstop filter array 94 is shown in series with the lead body 96. This can in turn be connected to the cuff electrode 88 of FIG. 9 or to the multiple cuff electrodes 74, 80 illustrated in FIGS. 6 and 7. It can also be adapted to the multiple single electrodes illustrated in FIG. 11. The multiple bandstop chip as illustrated in FIGS. 10 and 11 can be made in a variety of ways utilizing the technology disclosed in U.S. patent application Ser. Nos. 11/558,349, and 60/968,662, by putting the devices on a substrate next to each other on each lead wire. The structure shown in FIGS. 10 and 11 can be over-molded with silicone or the like to provide reliable mechanical attachment and protection from body fluids.

FIG. 12 is taken generally along the line 12-12 from FIG. 10, and illustrates one of many ways to form a multiple array 98 of bandstop filter chips. One can see that there is a thin substrate 100 which can be of alumina or any other substrate material known in the prior art. Different types of bandstop filters 102a-f (MRI chips) are shown by way of illustrating that there are many ways to construct this multiple array 98. Referring to drawings from U.S. patent application Ser. No. 11/558,349, the MRI chips 102a-f are similar to FIGS. 80-85 and FIG. 136 (which is thick film deposited right on the substrate). Those skilled in the art will realize that imbedded or MEMs components can also be used to form the multiple bandstop MRI filter array 98. In addition, multilayer substrates may be used to increase packaging density. Wirebond pads 104, leadwires 106 and 106' and electrical connections 108 (typically laser welds or gold wirebonds), are also shown. The bandstop filter chips 102a-f have end terminations 110 as shown. There are electrical connections from these end terminations 110 to the circuit traces 112. The entire assembly is desirably over coated, over molded (with silicone or the like), or glass encapsulated to enhance mechanical strength and biocompatibility.

Figure 13:
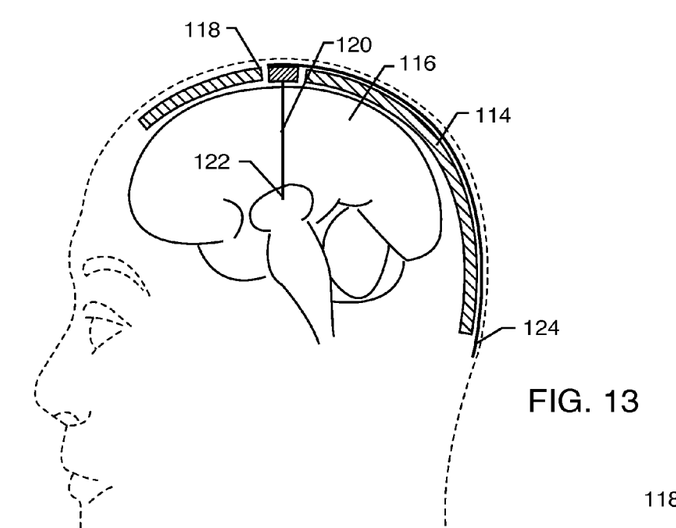
FIG. 13 is a diagrammatic, side cross-sectional view of the human head showing the placement of a deep brain probe and electrode embodying the bandstop filter of the present invention.

FIG. 13 is a diagrammatic side cross-sectional view of the human head showing the skull 114 and the brain 116. A burr hole 118 is drilled through the skull 114 for placement of deep brain probe 120 with associated electrodes 122. One can see that there is a lead wire body 124 which has been tunneled up underneath the skin and attaches to the deep brain probe 120. One or more bandstop filter chips of the present invention are located inside of the skull burr hole 118.

Figure 14:
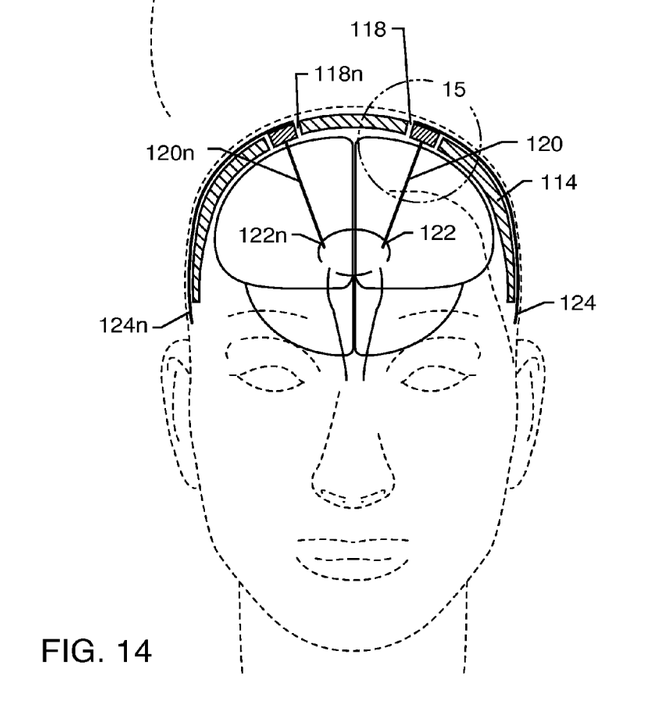
FIG. 14 is a diagrammatic, front cross-sectional view of the human head showing use of multiple deep brain probes.

FIG. 14 is a diagrammatic cross-sectional front view of the human head, showing that there can be multiple deep brain probes 120 . . . 120$_n$ placed as previously described in connection with FIG. 13. In a preferred embodiment, the top of the deep brain probe 120 and associated bandstop filter would be flush with the top of the skull 114. The lead wire 124 is generally connected to a pulse generator or transmitter which is either implanted or can sit outside the skin. There can also be a receiver which sits on the skin. The deep brain probe 120 can also have a nail head or nail shank.

Figure 15:
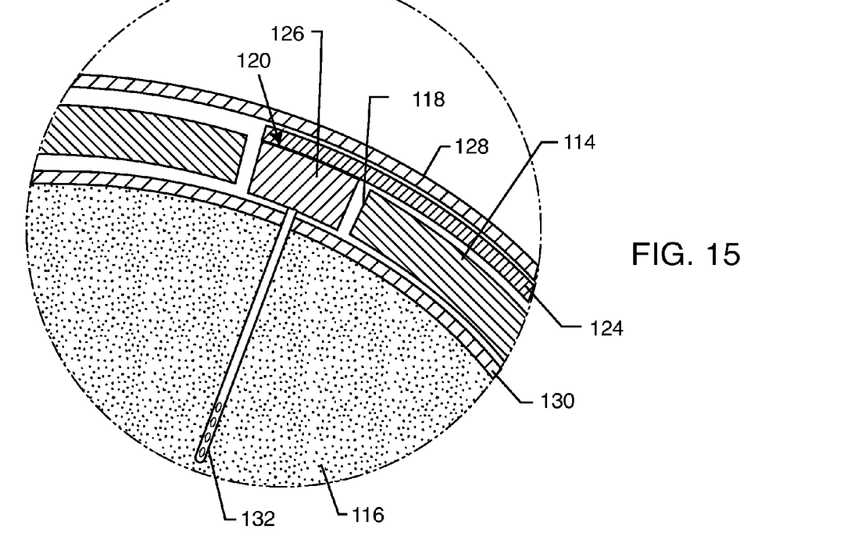
FIG. 15 is an enlarged sectional view taken generally of the area indicated by the line 15 in FIG. 14.

FIG. 15 is an elongated sectional view of the area indicated by line 15 in FIG. 14, of the deep brain probe 120. Shown is the location of the bandstop filter 126, the skin 128 which covers the skull 114, the lead wire 124, the burr hole 118, dura layer 130 and the brain 116. At the end of the deep brain probe 120 are electrodes 132.

Figure 16:
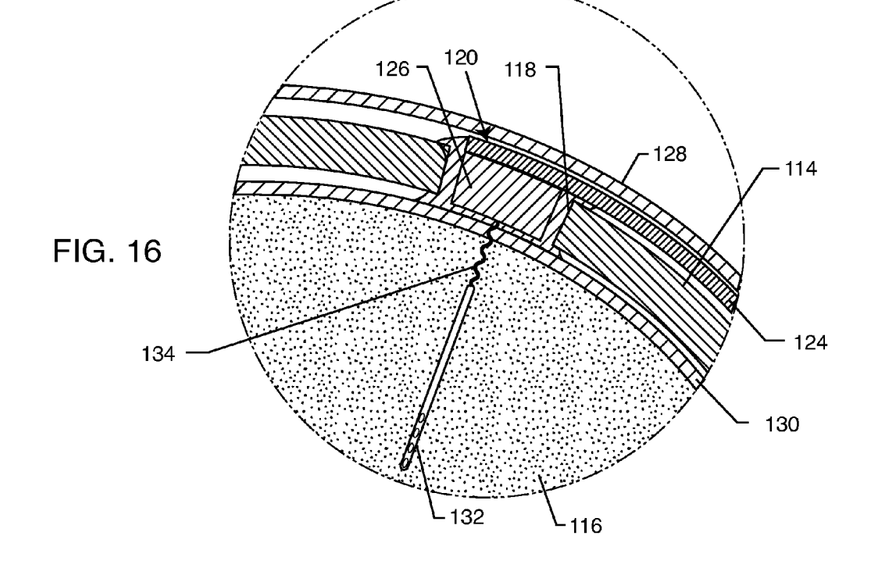
FIG. 16 is a view similar to FIG. 15, illustrating an alternative probe and electrode arrangement.

FIG. 16 illustrates an alternative view wherein a highly flexible region 134 is connected between the bandstop filter 126 and the electrodes 132. This flexible section 134 accounts for the relative motion between the skull 114 and the brain 116.

Figure 17:
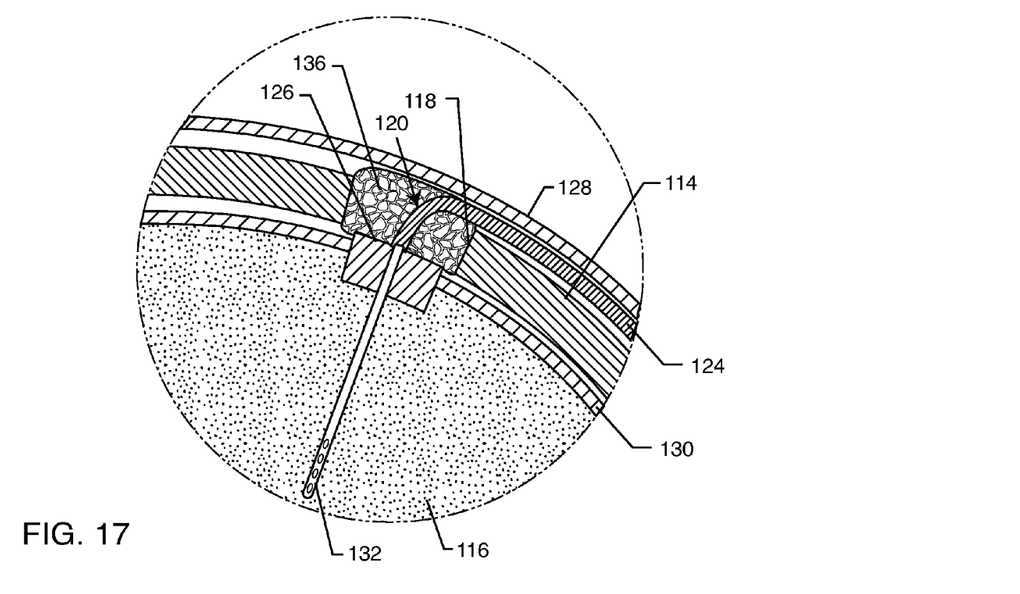
FIG. 17 is a sectional view similar to FIG. 15, except that the probe containing the bandstop filter chip is embedded under the skull and then the skull bore hole is covered with a bone encapsulant.

FIG. 17 illustrates an alternate configuration taken from FIG. 15 wherein the top of the bandstop filter 126 is below the skull bone 114. The burr hole 118 is covered with a bone encapsulant 136. It will be obvious to those skilled in the art that the deep brain probe 120 of the present invention can be placed in various locations that are convenient for the physician/surgeon.

In all of the previously described embodiments, it is important that the bandstop filter be as close to the electrode-to-tissue interface as possible. The reason for this is that lead wire systems act as transmission lines in that they have series inductance and resistance and also stray capacitance from lead to lead. This tends to cause them to decouple into various loops at MRI pulsed frequencies. It is for this reason, for example in a cardiac pacemaker, that placing a bandstop filter at the housing of the cardiac pacemaker will not provide adequate cooling at the end of, for example, a 52 cm lead wire whose electrode tip is inside, for example, the right ventricle. The impedance of the lead wire would tend to decouple the bandstop filter by presenting a very high impedance at the MRI RF pulsed frequencies. Accordingly, it is a feature of the present invention that the bandstop filter be placed in relatively close proximity to the delivery electrodes as illustrated in the accompanying drawings.

This principle varies with the RF pulsed frequency of the MRI machine. For example, a 0.5 Tesla machine has an RF pulsed frequency of 21 MHz. In this case, the wavelength is long enough where the bandstop filter could be a considerable distance away from the delivery electrode and still be quite effective. However, when one gets up around 3 Tesla with an RF pulsed frequency of 128 MHz, then the bandstop filter must be much closer to the delivery electrode. This is because the impedance along the series lead wire tend to increase at higher frequencies. In the present invention, in all cases, the bandstop filter is no more than 15 cm away from the delivery electrode. This will provide effective reduction in current flow at the MRI pulsed frequency thereby providing effective cooling at the distal electrode tips.

Figure 18:
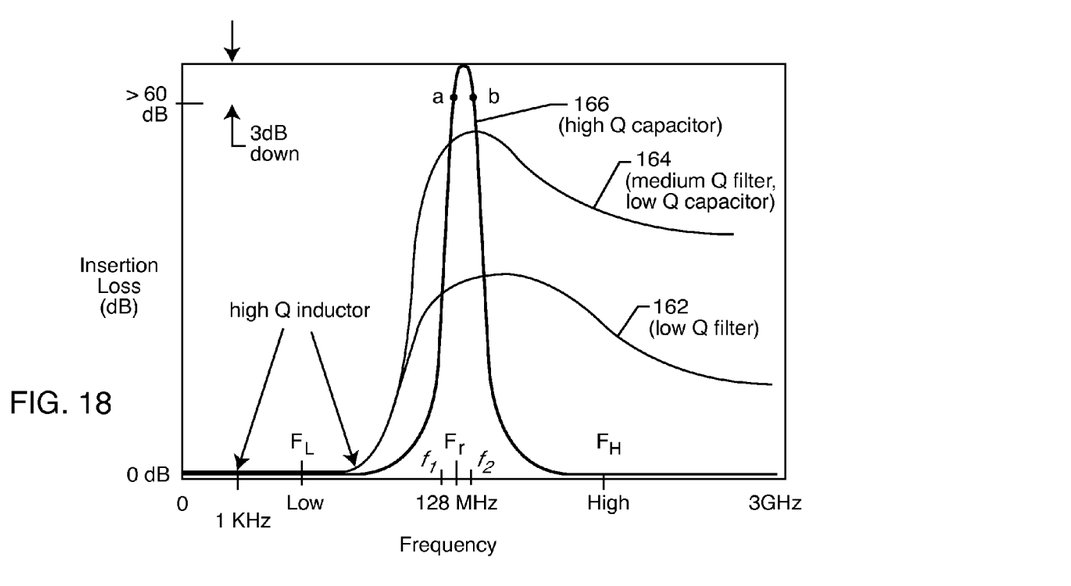
FIG. 18 is a graph of insertion loss verses frequency for bandstop filters having differing quality "Q" factors.

Referring now to FIG. 18, the efficiency of the overall bandstop circuits (38, 70, 86, 102) previously discussed herein are also measured in terms of a quality factor, Q, although this factor is defined differently than the one previously mentioned for discrete capacitors and inductors. The circuit Q is typically expressed using the following equation:

$$Q = \frac{f_r}{\Delta f_{3dB}}$$

Where $f_r$ is the resonance frequency, and $\Delta f_{3dB}$ shown as points a and b in FIG. 18, is the bandwidth of the bandstop filter. Bandwidth is typically taken as the difference between the two measured frequencies, $f_1$ and $f_2$, at the 3 dB loss points as measured on an insertion loss chart, and the resonance frequency is the average between $f_1$ and $f_2$. As can be seen in this relationship, higher Q values result in a narrower 3 dB bandwidth.

Material and application parameters must be taken into consideration when designing bandstop filters. Most capacitor dielectric materials age 1%-5% in capacitance values per decade of time elapsed, which can result in a shift of the resonance frequency of upwards of 2.5%. In a high-Q filter, this could result in a significant and detrimental drop in bandstop performance. A low-Q filter would minimize the effects of resonance shift and would allow a wider frequency band through the filter. However, low Q filters also display lower than desirable attenuation behavior at the desired bandstop frequency (see FIG. 18, curve 162). For this reason, the optimum Q for the bandstop filter of the present invention will embody a high Q inductor L and a relatively low Q capacitor C which will result in a medium Q bandstop filter as shown in curve 164 of FIG. 18.

Accordingly, the "Q" or quality factor of the bandstop circuit is very important. As mentioned, it is desirable to have a very low loss circuit at low frequencies such that the biological signals not be undesirably attenuated. The quality factor not only determines the loss of the filter, but also affects its 3 dB bandwidth. If one does a plot of the filter response curve (Bode plot), the 3 dB bandwidth determines how sharply the filter will rise and fall. With reference to curve 166 of FIG. 18, for a bandstop that is resonate at 128 MHz, an ideal response would be one that had infinite attenuation at 128 MHz, but had zero attenuation at low frequencies below 1 KHz. Obviously, this is not possible given the space limitations and the realities of the parasitic losses within components. In other words, it is not possible (other than at cryogenic temperatures) to build an inductor that has zero internal resistance. On the other hand, it is not possible to build a perfect (ideal) capacitor either. Capacitors have internal resistance known as equivalent series resistance and also have small amounts of inductance. Accordingly, the practical realization of a circuit, to accomplish the purposes of the present invention, is a challenging one. This is particularly true when one also considers that the bandstop circuit must also be miniature, highly reliable, and completely biocompatible.

The performance of the circuit is directly related to the efficiency of both the inductor and the capacitor; the less efficient each component is, the more heat loss that results, and this can be expressed by the addition of resistor elements to the ideal circuit diagram. The effect of lower Q in the bandstop circuit is to broaden the resonance peak about the resonance frequency. By deliberately using a low Q capacitor, one can broaden the resonance such that relatively high impedance (high attenuation) is presented at multiple MRI RF frequencies, for example 64 MHz and 128 MHz.

Referring again to FIG. 18, one can see curve 164 wherein a high Q inductor has been used in combination with a low Q capacitor. This has a very desirable effect in that at very low frequencies, the impedance of the bandstop circuit 146 is essentially zero (below 1 ohm) ohms (or zero dB loss). This means that biologic frequencies are not undesirably attenuated. However, one can see that the 3 db bandwidth is much larger. This is desirable as it will block multiple RF frequencies. As one goes even higher in frequency, curve164 will desirably attenuate other high frequency EMI signals, such as those from cellular telephones, microwave ovens and the like. Accordingly, it is often desirable that very low loss inductors be used in combination with relatively high loss capacitors to achieve a medium or lower Q bandstop filter. Again referring to FIG. 18, one can see that if the Q of the overall circuit or of the individual components becomes too low, then we have a serious degradation in the overall attenuation of the bandstop filter. Accordingly, a careful balance between component design and bandstop circuit Q must be achieved.

Although several embodiments of the invention have been described in detail for purposes of illustration, various modifications of each may be made without departing from the spirit and scope of the invention. Accordingly, the invention is not to be limited, except as by the appended claims.

What is claimed is:

1. A medical lead system, comprising:
   a lead wire configured for insertion into a venous system or tunneled through biological tissue, connecting at one end to an implantable medical device, and at an opposite end to an electrode in contact with biological cells; and
   a bandstop filter associated with the lead wire, for attenuating current flow through the lead wire over a range of frequencies, the bandstop filter having an overall circuit Q wherein the resultant 3db bandwidth is on the order of MHz, and wherein the bandstop filter comprises a capacitor in parallel with an inductor, said parallel capacitor and inductor placed in series with the lead wire, wherein values of capacitance and inductance are selected such that the bandstop filter is resonant at a selected center frequency.

2. The system of claim 1, wherein the range of frequencies comprises a plurality of MRI pulsed frequencies.

3. The system of claim 1, wherein the lead wire comprises a proximal section extending from the terminal pin, and a reduced-diameter distal section, and wherein the bandstop filter is disposed between the proximal and distal sections.

4. The system of claim 1, wherein the bandstop filter includes fixation tines for fixing the bandstop filter in a desired location within the venous system.

5. The system of claim 1, wherein the lead wire comprises an epicardial lead.

6. The system of claim 5, wherein the epicardial lead incorporates the bandstop filter therein.

7. The system of claim 1, wherein the lead wire comprises a split cylinder cuff electrode.

8. The system of claim 7, wherein the split cylinder cuff electrode incorporates the bandstop filter therein.

9. The system of claim 1, wherein the lead wire comprises self-sizing nerve cuffs.

10. The system of claim 9, wherein the self-sizing nerve cuffs incorporate the bandstop filter therein.

11. The system of claim 1, wherein the lead wire comprises a multiple-cuff nerve electrode.

12. The system of claim 11, wherein the multiple-cuff nerve electrode incorporates multiple bandstop filters therein.

13. The system of claim 1, wherein the bandstop filter comprises a multiple bandstop filter array.

14. The system of claim 13, wherein the multiple bandstop filter array comprises a plurality of bandstop filter chips disposed on a substrate.

15. The system of claim 14, wherein at least one of the bandstop filter chips is thick-film deposited onto the substrate.

16. The system of claim 1, wherein the lead wire comprises a deep brain probe.

17. The system of claim 16, wherein the deep brain probe incorporates the bandstop filter therein.

18. The system of claim 17, including a flexible conductor disposed between the bandstop filter and the electrode.

19. The system of claim 17, wherein the deep brain probe is either flush with the skull, recessed, or subdural.

20. A medical lead system, comprising:
   a lead wire having a proximal end, and an electrode in contact with biological cells at a distal end; and
   a bandstop filter associated with the lead wire, for attenuating current flow through the lead wire over a range of frequencies, the bandstop filter having an overall circuit Q wherein the resultant 3db bandwidth is on the order of MHz, and wherein the bandstop filter comprises a capacitor in parallel with a conductor, said parallel capacitor and inductor placed in series with the lead wire wherein values of capacitance and inductance are selected such that the bandstop filter is resonant at a selected center frequency.

21. The system of claim 20, wherein the lead wire comprises an epicardial lead, a split-cylinder cuff electrode, self-sizing nerve cuffs, a multiple-cuff nerve electrode, a multiple bandstop filter array, or a deep brain probe.

22. The system of claim 21, wherein the epicardial lead, the split-cylinder cuff electrode, the self-sizing nerve cuffs, the multiple-cuff nerve electrode, or the deep brain probe incorporates the bandstop filter therein.

23. The system of claim 21, wherein the multiple bandstop filter array comprises a plurality of bandstop filter chips disposed on a substrate.

24. The system of claim 23, wherein at least one of the bandstop filter chips is thick-film deposited onto the substrate.

25. The system of claim 21, wherein the bandstop filter is disposed adjacent to the electrode.

* * * * *

UNITED STATES PATENT AND TRADEMARK OFFICE
Certificate

Patent No. 7,899,551 B2                                                         Patented: March 1, 2011

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Randy Westlund, River Falls, WI (US); Robert A. Stevenson, Canyon Country, CA (US); Christine A. Frysz, Orchard Park, NY (US); Warren S. Dabney, Orchard Park, NY (US); and Henry R. Halperin, Pikesville, MD (US).

Signed and Sealed this Third Day of January 2012.

NIKETA PATEL
*Supervisory Patent Examiner*
Art Unit 3762
Technology Center 3700